United States Patent
Gutierrez et al.

(10) Patent No.: US 11,129,563 B2
(45) Date of Patent: Sep. 28, 2021

(54) EYE-MOUNTABLE DEVICE WITH MUSCLE SENSOR

(71) Applicant: Verily Life Sciences LLC, South San Francisco, CA (US)

(72) Inventors: Christian Gutierrez, Pacifica, CA (US); Shivkumar Sabesan, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 120 days.

(21) Appl. No.: 16/373,533

(22) Filed: Apr. 2, 2019

(65) Prior Publication Data

US 2019/0307399 A1 Oct. 10, 2019

Related U.S. Application Data

(60) Provisional application No. 62/652,678, filed on Apr. 4, 2018.

(51) Int. Cl.
*G02C 7/00* (2006.01)
*G02C 5/00* (2006.01)
(Continued)

(52) U.S. Cl.
CPC .............. *A61B 5/389* (2021.01); *A61B 5/296* (2021.01); *A61B 5/398* (2021.01); *A61B 5/6821* (2013.01);
(Continued)

(58) Field of Classification Search
CPC ... A61B 3/1005; A61B 5/14532; A61B 3/113; A61B 3/103; A61B 3/14; A61B 3/125;
(Continued)

(56) References Cited

U.S. PATENT DOCUMENTS 8,172,900 B2 5/2012 Roberts et al.
9,052,528 B2 6/2015 Pugh et al.
(Continued)

OTHER PUBLICATIONS

Notification of Transmittal of the International Search report and Written Opinion for corresponding international application No. PCT/US2019/025825 dated Sep. 10, 2019, 16 pages.
(Continued)

*Primary Examiner* — Dawayne Pinkney
(74) *Attorney, Agent, or Firm* — Christensen O'Connor Johnson Kindness PLLC

(57) ABSTRACT

An ophthalmic device includes an enclosure, an electromyography sensor, and a controller. The enclosure is configured to mount in or on an eye. The enclosure further includes a first material and a second material disposed within the first material. The electromyography sensor is adapted to measure electrical activity of a muscle of the eye proximate to a first annular region of the ophthalmic device when the ophthalmic device is mounted in or on the eye. The electromyography sensor includes a first electrode and a second electrode, each positioned within the first annular region between the first material and at least a portion of the second material. The controller, coupled to the electromyography sensor, stores instructions that when executed causes the ophthalmic device to perform operations including acquiring a first signal representative of the electrical activity of the muscle by measuring the electrical activity with the electromyography sensor.

26 Claims, 9 Drawing Sheets

(51) Int. Cl.
- *G02C 7/02* (2006.01)
- *G02C 3/00* (2006.01)
- *A61B 5/389* (2021.01)
- *A61F 2/72* (2006.01)
- *G02C 7/08* (2006.01)
- *A61B 5/00* (2006.01)
- *G02C 7/04* (2006.01)
- *A61B 5/296* (2021.01)
- *A61B 5/398* (2021.01)
- *A61F 2/16* (2006.01)

(52) U.S. Cl.
CPC .................. *A61F 2/72* (2013.01); *G02C 7/04* (2013.01); *G02C 7/083* (2013.01); *A61B 2562/0215* (2017.08); *A61B 2562/04* (2013.01); *A61F 2/1624* (2013.01)

(58) Field of Classification Search
CPC ..... A61B 3/1225; A61B 3/024; A61B 3/1015; A61B 3/107; G02C 5/00; G02C 7/04; G02C 7/02; G02C 7/06; G02C 7/08
USPC ...... 351/159.01–159.03, 41, 159.05, 159.39, 351/159.73–159.77, 178, 200, 205–206, 351/209–210, 221–222, 245–247; 600/319

See application file for complete search history.

(56) References Cited

U.S. PATENT DOCUMENTS

| | | | |
|---|---|---|---|
| 9,144,376 B2 | 9/2015 | Guth et al. | |
| 9,226,818 B2 | 1/2016 | Campin et al. | |
| 9,241,669 B2 | 1/2016 | Pugh et al. | |
| 9,468,372 B2 | 10/2016 | Pugh et al. | |
| 9,690,116 B2 | 6/2017 | Pugh et al. | |
| 2013/0184815 A1* | 7/2013 | Roholt | A61F 2/1635 623/6.22 |
| 2013/0282117 A1 | 10/2013 | Van Heugten et al. | |
| 2014/0192318 A1 | 7/2014 | Guth et al. | |
| 2015/0173893 A1 | 6/2015 | Portney | |
| 2017/0049395 A1 | 2/2017 | Cao | |
| 2017/0079771 A1 | 3/2017 | Roholt et al. | |
| 2018/0031865 A1 | 2/2018 | Hyde et al. | |

OTHER PUBLICATIONS

Schaeffel, F. et al., "Inter-Individual Variability in the Dynamics of Natural Accommodation in Humans: Relation to Age and Refractive Errors", Journal of Physiology 461, 1993, pp. 301-320.

Strenk, S. et al., "Age-Related Changes in Human Ciliary Muscle and Lens: A Magnetic Resonance Imaging Study", Investigative Ophthalmology & Visual Science, vol. 40, No. 6, May 1999, 8 pages.

Pardue, M. et al., "Age-Related Changes in Human Ciliary Muscle", Ophthalmology & Visual Science, vol. 77, No. 4, 2000, 7 pages.

Kasthurirangan, S. et al., "Characteristics of Pupil Responses During Far-to-Near and Near-to-Far Accommodation", Ophthal. Physiol. Opt. vol. 25, 2005, 12 pages.

Invitation to Pay Additional Fees, as issued by the International Searching Authority, for corresponding international application No. PCT/US2019/025825, dated Jul. 16, 2019, pp. 1-13.

* cited by examiner

EYE-MOUNTABLE DEVICE WITH MUSCLE SENSOR

CROSS-REFERENCE TO RELATED APPLICATIONS

This application claims the benefit of U.S. Provisional Application No. 62/652,678, filed Apr. 4, 2018, which is hereby incorporated by reference in its entirety.

TECHNICAL FIELD

This disclosure relates generally to the field of wirelessly connected biometric sensors, and in particular but not exclusively, relates to contact lenses.

BACKGROUND INFORMATION

Contact lenses are worn by a large number of people throughout the world, mainly for the purpose of vision correction. However, as lens technology continues to progress, the functionality of contact lenses may extend beyond merely providing static vision correction to other areas. For example, eye-mountable devices (EMD), smart contact lenses, or intraocular lenses, may offer unique opportunities in health monitoring, biometric sensing, dynamic vision correction, and other types of vision augmentation.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
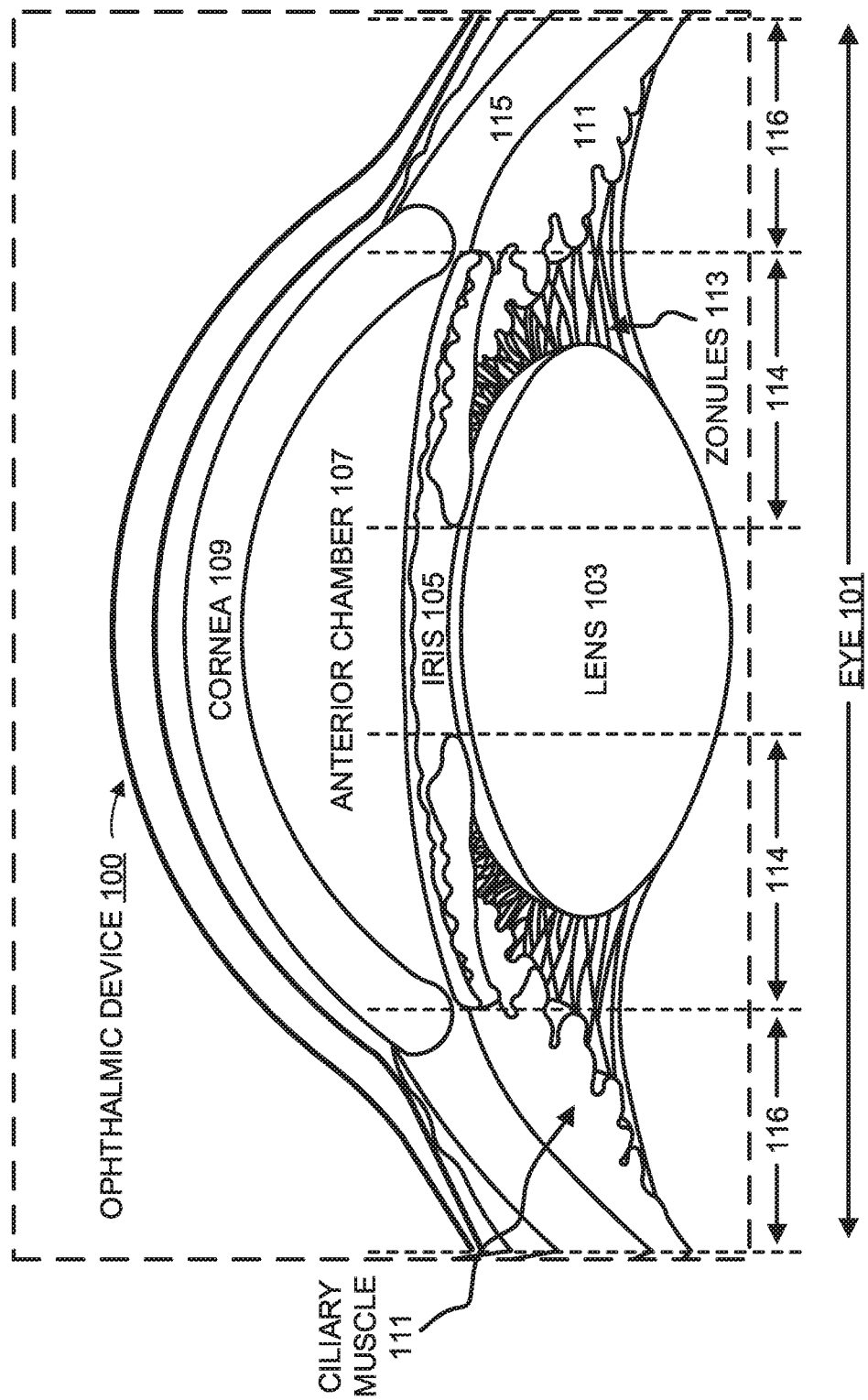
FIG. 1 illustrates a cross-sectional view of an ophthalmic device with muscle sensor mounted on an eye of a user, in accordance with an embodiment of the disclosure.

Embodiments of ophthalmic devices with muscle sensor are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Ocular accommodation is the ability of the eye's lens to dynamically change focus. This ability begins to diminish in most people by age forty due to a natural loss of elasticity of the crystalline lens resulting in an inability for the eye to adjust or accommodate its refractive power in response to changes in viewing distance. This condition is known as presbyopia and typically manifests first in a loss of ability to read clearly. Traditional contact lens may be ineffective at correcting vision problems caused by presbyopia as they typically only provide static vision correction. Devices that provide dynamic vision correction may mitigate the effects of presbyopia. However, dynamically correlating an accommodation effort by a user of the device to a specific degree of vision correction remains a significant challenge.

Described herein are embodiments of ophthalmic devices (e.g. eye-mountable devices, smart contact lenses, intraocular lenses, and the like) capable of providing dynamic vision correction by electrically detecting physiological activation of one or more muscles of the eye associated with an accommodative effort. In some embodiments, the detected physiological activation is represented as an electrical signal that may be utilized for closed-loop control of the ophthalmic device to provide dynamic vision correction based on a user's accommodative effort. In this regard, the electrical signals acquired by detecting electrical activity of muscles associated with an accommodative effort (e.g., engagement of the iris, activation of the ciliary muscle, and the like) are utilized to dynamically correlate the accommodative effort of the user with a specific degree of vision correction. For example, an unfocused foveal image and binocular disparity are the primary stimuli that elicit an accommodative response or effort. The accommodative response is characterized by muscular adjustments of the eye including, constriction of the ciliary muscle and release of tension on zonule fibers, constriction of the iris sphincter, and contraction of the medial rectus muscle to converge the eyes. Measurement of electrical activity of these muscles may be utilized to determine a level of accommodative effort. Advantageously, these embodiments do not rely on mechanical movement of constituents of the eye (e.g., the capsular bag) to determine the accommodative effort, but rather derive information based on the underlying physiology of the eye itself.

FIG. 1 illustrates a cross-sectional view of an ophthalmic device 100 with muscle sensor mounted on an eye 101 of a user, in accordance with an embodiment of the disclosure. The ophthalmic device 100 utilizes one or more extraocular electromyography (EMG) sensors to measure electrical activity of muscles of the eye 101 associated with an accommodative effort. Depending on the muscles of the eye 101 being targeted for measurement, the dimensions of the ophthalmic device 100 may vary. As illustrated, the ophthalmic device 100 is larger than a traditional contact lens and extends beyond cornea 109 to sclera 115 of the eye 101. In other embodiments, the ophthalmic device 100 may have substantially similar dimensions of a traditional contact lens and, for example, may only cover part of the cornea 109.

In some embodiments, the ophthalmic device 100 may include an iris EMG sensor to measure electrical activity of the eye 101. The pupil (e.g., the hole at the center of iris 105) is the opening through which light enters the eye 101 and begins the process of visual perception. The diameter of that opening is dictated by the relative contraction of two opposing sets of muscles within the iris 105, the sphincter and dilator pupillae. The size of the diameter of the opening of the iris 105 is determined primarily in response to light and accommodation reflexes. The fibers of the iris sphincter muscle (e.g., the sphincter pupillae) are arranged concentrically and utilized for constriction of the pupil (e.g., iris constriction). The dilator muscles (e.g., the dilator pupillae) are arranged radially, and emanate from the pupil center outwards like spokes of a bicycle wheel. Contractions of dilator muscle fibers serve to enlarge the diameter of the pupil and reduce iris extension. While some pupillary movements are also known to be coupled to cognitive processes, the magnitudes of these movements are thought to be lower in level relative to pupillary movements that occur due to light reflex and accommodation.

More specifically, the act of focusing the eye to different distances (e.g., different levels of accommodation) is associated with a concurrent change in pupil diameter. For example, in humans the pupil diameter can vary from less than 1 mm to more than 9 mm. The pupil diameter decreases when focusing from far-to-near and increases when focusing from near-to-far. In general, the average pupil diameter change per diopter of accommodation is 0.39 mm per diopter, which is greater than the average change of disaccommodation of 0.17 mm per diopter. Thus monitoring or measuring the electrical activity of the iris muscles (e.g., the sphincter and dilator pupillae of the iris 105) may be used to determine the level of accommodative effort.

In the same or other embodiments, the ophthalmic device 100 may include a ciliary EMG sensor to measure electrical activity of ciliary muscle 111 of the eye 101. The ciliary muscle 111 adjusts the shape of lens 103 to achieve accommodation and is predominantly comprised of two fiber bundles that are distinguished by their geometry. Fibers that extend radially (e.g., Brucke fibers) and those that are circular (e.g., Muller fibers) form a sphincter-like structure around the lens 103. The density and distribution of these fibers within the ciliary muscle 111 have been shown to vary with age. However, it is known that generally the radial fibers form sixty to eighty percent of the ciliary muscle 111 area, while the circular fibers range in four to twenty four percent of the ciliary muscle 111 area. Both of these fiber bundles are involved in the accommodation process and as such provide geometrically distinct targets for the ciliary EMG sensor.

The EMG sensor (e.g., the iris EMG sensor or the ciliary EMG sensor) included in the ophthalmic device 100 may be positioned within the ophthalmic device 100 to target specific iris and/or ciliary muscles. On average the inner diameter of the iris 105 is about 4 mm and extends out the iris plant that is closely coupled to the ciliary body at about 13.1 mm in diameter. Therefore, annulus 114 defined by the region between the diameters of about 4 mm to 13.1 mm form the inner and outer rims of the iris 105. Annulus 114 represents a region for the iris EMG sensor to target for measuring the electrical activity of the muscles associated with the iris 105 of the eye 101 that respond to an accommodative effort. Similarly, annulus 116 represents a region for the ciliary EMG sensor to target for measuring the electrical activity of muscles associated with the ciliary muscle 111 of the eye that respond to an accommodative effort. On average the inner diameter of the ciliary muscle 111 is 13.1 mm and continues to contract with accommodative effort, even for advanced presbyopes. The mean length of the ciliary muscle is expected to be 3.9 mm. Therefore the annulus 116 defined by the region between the diameters of about 13.1 mm and 20.9 mm form the inner and outer rims of the ciliary muscle 111 and is the primary target for the ciliary EMG sensor.

Figure 2:
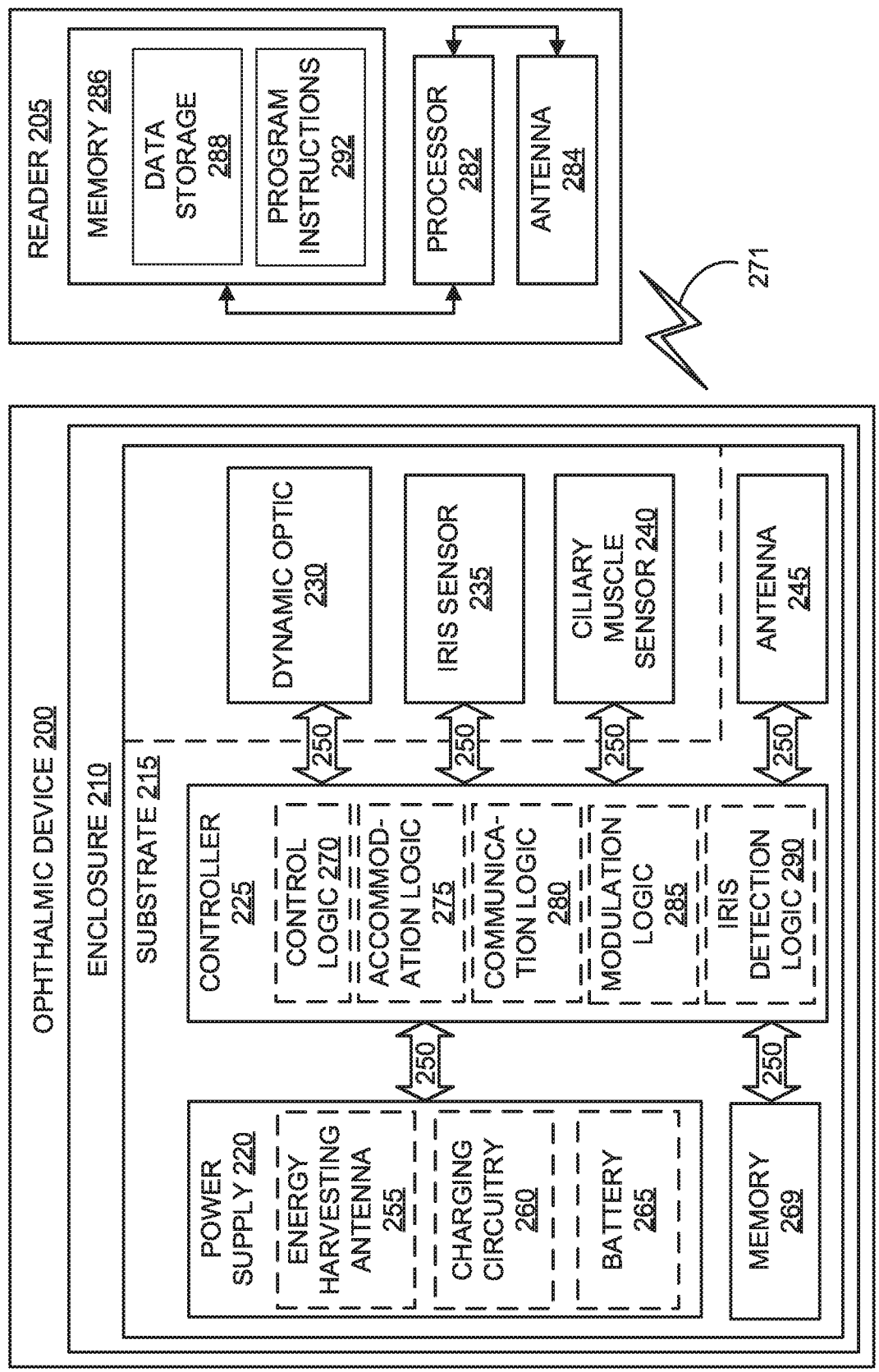
FIG. 2 illustrates a functional block diagram of an ophthalmic device with muscle sensor along with an external reader, in accordance with an embodiment of the disclosure.

FIG. 2 illustrates a functional block diagram of an ophthalmic device 200 with muscle sensor along with an external reader 205, in accordance with an embodiment of the disclosure. Ophthalmic device 200 is one possible implementation of the ophthalmic device 100 illustrated in FIG. 1. Referring back to FIG. 2, the exposed portion of the ophthalmic device 200 includes an enclosure 210 formed to be contact-mounted to a corneal surface, sclera, or other portion of an eye a user. Alternatively, ophthalmic device 200 may be disposed within the eye of the user. Substrate 215 is embedded within or surrounded by the enclosure 210 and provides a mounting surface for a power supply 220, a controller 225 (with circuitry and/or logic), a dynamic optic 230, an iris sensor 235, a ciliary muscle sensor 240, antenna 245, memory 269, and various interconnects 250 coupling the constituent components together. The illustrated embodiment of power supply 220 includes an energy harvesting antenna 255, charging circuitry 260, and battery/capacitor 265. The illustrated embodiment of controller 225 includes control logic 270, accommodation logic 275, and communication logic 280, modulation logic 285, and iris detection logic 290. The illustrated embodiment of reader 205 includes a processor 282, an antenna 284, and memory 286. The illustrated embodiment of memory 286 includes data storage 288 and program instructions 290.

Controller 225 is coupled to acquire and/or receive signals from iris sensor 235 and/or ciliary muscle sensor 240 representative of electrical activity of muscles associated with accommodative effort of the eye. For example, the iris sensor 235 and or ciliary muscle sensor 240 may be an electromyography sensor. The controller 225 is further coupled to operate dynamic optic 230 based on the acquired signals to provide a level of accommodation to the eye. The dynamic optic 230 may be an electro-active accommodating optic that adjusts an index of refraction in response to an applied voltage or electrical field. The dynamic optic 230 may be a liquid crystal optic, an electrowetting optic, or any other electro-active adjustable optic to adjust an index of refraction. Power supply 220 supplies operating voltages to the controller 225, dynamic optic 230, iris sensor 235, ciliary muscle sensor 240, and the like. Antenna 245 is operated by the controller 225 to communicate information to and/or from the ophthalmic device 200. In one embodiment, antenna 245, controller 225, power supply 220, iris sensor 235, and ciliary muscle sensor 240 are all situated on the substrate 215. In one embodiment, the dynamic optic 230 is embedded within the enclosure 210, but is not disposed on substrate 215. Similarly, the iris sensor 235 and the ciliary muscle sensor 240 are embedded within the enclosure 210 but are not necessarily disposed on the substrate 215. Because ophthalmic device 200 includes electronics and is configured to be contact-mounted to or disposed within an eye, it is also referred to herein as an ophthalmic electronics platform, eye-mountable device, contact lens, smart contact lens, or intraocular lens.

To facilitate contact-mounting, the enclosure 210 may have a concave surface configured to adhere ("mount") to a moistened corneal surface (e.g., by capillary forces with a tear film coating the corneal surface). Additionally or alternatively, the ophthalmic device 200 may be adhered by a vacuum force between the corneal surface and the enclosure 210 due to the concave curvature. While mounted with the concave surface against the eye, the outward-facing surface of the enclosure 210 may have a convex curvature that is formed to not interfere with eye-lid motion while the ophthalmic device 200 is mounted to the eye. For example, the enclosure 210 may be a substantially transparent curved disk shaped similarly to a contact lens.

The enclosure 210 may include one or more biocompatible materials, such as those employed for use in contact lenses or other ophthalmic applications. The enclosure 210 may optionally be formed in part from such biocompatible materials or may include an outer coating with such biocompatible materials. The enclosure 210 may include materials configured to moisturize the corneal surface, such as hydrogels and the like. In some instances, the enclosure 210 may be a deformable ("non-rigid") material to enhance wearer comfort. In some instances, enclosure 210 may be shaped to provide a predetermined, vision-correcting optical power, such as can be provided by a contact lens. The enclosure 210 may be fabricated of various materials including a polymeric material, polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate), silicone elastomer, or combinations of these, or otherwise.

In some embodiments, the enclosure material includes one or more materials. For example, the enclosure 210 may include at least two polymeric materials, a soft exterior (first material) to be mounted to the corneal or scleral surface and a rigid center material (second material). The rigid center material may contain active electronics (e.g., the power supply 220, the controller 225, and the like) while the soft lens material may be flexible and/or soft for the ocular comfort of the user. It is appreciated, that in some embodiments, the substrate 215 may be omitted and the rigid center material may provide structural support to the various electronic components of the ophthalmic device 200. The soft lens material may include silicone or silicone-based hydrogels and fully encapsulate the rigid lens material. The rigid lens material may include PMMA, rigid gas permeably polymers, rigid silicone and the like. The rigid center material may have minimal hydration while the soft lens material may have a significant degree of hydration such that the soft lens material has low impedance and high ionic conductivity.

The substrate 215 includes one or more surfaces suitable for mounting the iris sensor 235, the ciliary muscle sensor 235, the controller 225, the power supply 220, and the antenna 245. The substrate 215 may be employed both as a mounting platform for chip-based circuitry (e.g., by flip-chip mounting) and/or as a platform for patterning conductive materials (e.g., gold, platinum, palladium, titanium, copper, aluminum, carbon, silver, silver chloride, silver nanowires, nanowires, metals, other conductive materials, or combinations of these, etc.) to create electrodes, interconnects, antennae, etc. In some embodiments, substantially transparent conductive materials (e.g., indium tin oxide or metal nanowire mesh) may be patterned on substrate 115 to form circuitry, electrodes, etc. For example, the antenna 245 may be formed by depositing a pattern of gold or another conductive material on the substrate 215. Similarly, interconnect 250 may be formed by depositing suitable patterns of conductive materials on the substrate 215. A combination of resists, masks, and deposition techniques may be employed to pattern materials on the substrate 215. The substrate 215 may be a relatively rigid material, such as high molecular weight PMMA, polyethylene terephthalate ("PET"), Parylene C, Parylene HT, polyimide, polyurethane, polyimide, rigid gas permeable fluorosilicone acrylate, liquid crystal polymer, silicone-based polymers, silicon acrylate, or another material sufficient to structurally support the circuitry and/or electronics within the enclosure 210. The ophthalmic device 200 may alternatively be arranged with a group of unconnected substrates rather than a single substrate. For example, the controller 225 and power supply 220 may be mounted to a first substrate, while the antenna 245, the iris sensor 235, and the ciliary muscle sensor 240 may be mounted to one or more other substrates that are electrically connected to the first substrate via interconnects.

In some embodiments, the power supply 220, the controller 225, and the substrate 215, the iris sensor 235, and the ciliary muscle sensor 240 may be positioned away from the center of the ophthalmic device 200 and thereby avoid interference with light transmission to the eye through the center of the ophthalmic device 200. In contrast, the dynamic optic 230 may be centrally positioned to apply optical accommodation to the light transmitted to the eye through the center of the ophthalmic device 200. In some embodiments, the iris sensor 235 and the ciliary muscle sensor 240 include traces electrically coupled to one or more discrete electrodes that are positioned, for example, to measure electrical activity of muscles of the eye. In some embodiments, the iris sensor 235, the ciliary muscle sensor 240, and/or the substrate 215 may be substantially transparent to incoming visible light to mitigate interference with light transmission to the eye.

The substrate 215 may be shaped as a flattened ring with a radial width dimension sufficient to provide a mounting platform for the embedded electronics components. The substrate 215 may have a thickness sufficiently small to allow the substrate to be embedded in the enclosure 210 without adversely influencing the profile of the ophthalmic device 200. The substrate 215 may have a thickness sufficiently large to provide structural stability suitable for supporting the electronics mounted thereon. For example, the substrate 215 may be shaped as a ring with a diameter between around 4 millimeters to 21 millimeters and a thickness of about 50 micrometers or less. The radial width of the substrate 215 may be correlated to the targeted muscles of the eye being monitored for electrical activity.

In the illustrated embodiment, the power supply 220 includes the battery 265 to power the various embedded electronics, including the controller 225 and the dynamic optic 230. The battery 265 may be inductively charged by the charging circuitry 260 and the energy harvesting antenna 255. In some embodiments, the battery 265 may be a capacitor. The charging circuitry 260 may include a rectifier/regulator to condition the captured energy for charging the battery 265 or directly the power controller 225 without the battery 265. The charging circuitry 260 may also include one or more energy storage devices to mitigate high frequency variations in the energy harvesting antenna 255. For example, one or more energy storage devices (e.g., a capacitor, an inductor, etc.) may be connected to function as a low-pass filter.

The controller 225 contains logic to choreograph the operation of the other embedded components. The control logic 270 controls the general operation of the ophthalmic device 200, including providing a logical user interface, power control functionality, etc. Accommodation logic 275 includes logic for monitoring signals from the iris sensor 235 and the ciliary muscle sensor 2450, determining the focal distance of the user, and manipulating the dynamic optic 230 in response to provide the appropriate level of accommodation. Auto-accommodation of the ophthalmic device 200 may be implemented in real-time as a closed-loop system based upon the acquired signals from the iris sensor 235 and/or ciliary muscle sensor 240. More specifically, modulation logic 285 may be coupled to the ciliary muscle sensor 240 to interpret and analyze the signal acquired from the ciliary muscle sensor 240 while monitoring the electrical activity of the ciliary muscle. Similarly, the iris detection logic 290 may be coupled to the iris sensor 235 to interpret and analyze the signal acquired from the iris sensor 235 while monitoring the electrical activity of the muscles associated with the iris. The communication logic 280 provides communication protocols for wireless communication 271 with the reader 205 via the antenna 245.

It is noted that the block diagram shown in FIG. 2 is described in connection with functional modules for convenience in description, but does not necessarily connote physical organization. Rather, embodiments of the ophthalmic device 200 may be arranged with one or more of the functional modules ("sub-systems") implemented in a single chip, multiple chips, in one or more integrated circuits, or otherwise. For example, the various functional modules of the controller 225 may be implemented in software/firmware executed on a general purpose microprocessor, in hardware (e.g., application specific integrated circuit), or a combination of thereof. The controller, for example, may be coupled to or include the memory 269 to store instructions for execution by the controller 225. The instructions, when executed by the controller 225 may cause the ophthalmic device 200 to perform operations that correspond to the various functional modules of the controller 225. The memory 269 is a non-transitory computer-readable medium that may include, without limitation, a volatile (e.g. RAM) or non-volatile (e.g. ROM) storage system readable by the controller 225.

The external reader 205 includes antenna 284 (or group of more than one antennae) to send and receive the wireless signals 271 to and from the ophthalmic device 200. The external reader 205 also includes a computing system with processor 282 in communication with memory 286. The memory 286 is comparable to the memory 269 and is a non-transitory computer-readable medium readable by the processor 282. The memory 286 may also include program instructions 290 for execution by the processor 282 to cause the external reader 205 to perform processes specified by the instructions 290. For example, program instructions 290 may cause the external reader 205 to provide a user interface that allows for retrieving information communicated from the ophthalmic device 200 or allows transmitting information to the ophthalmic device 200 to program or otherwise select operational modes of the ophthalmic device 200. The external reader 205 may also include one or more hardware components for operating the antenna 284 to send and receive the wireless signals 271 to and from the ophthalmic device 200.

Figure 3A:
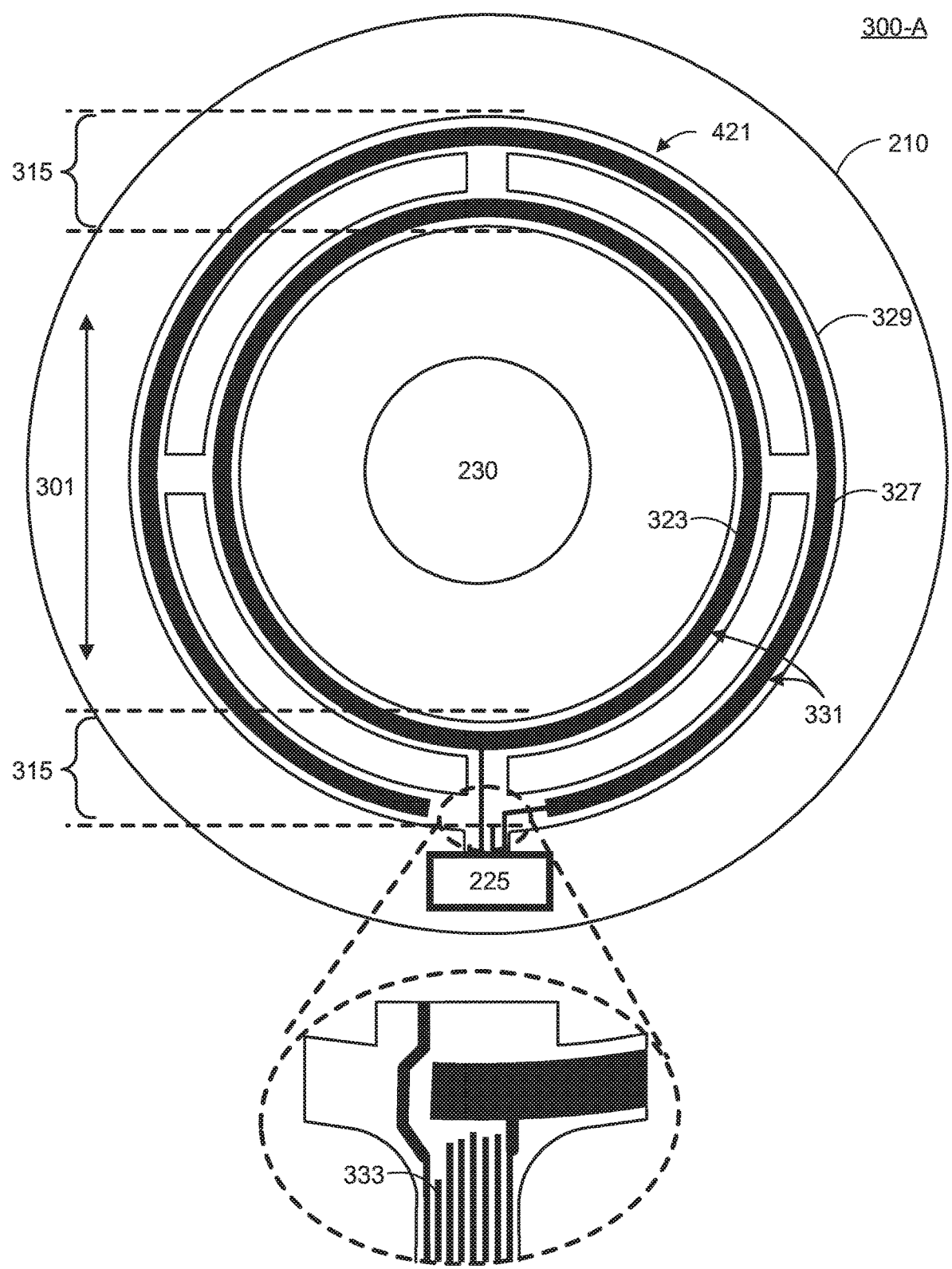
FIG. 3A illustrates a top view of an ophthalmic device with muscle sensor, in accordance with an embodiment of the disclosure.

FIG. 3A illustrates a top view of an ophthalmic device 300-A with muscle sensor 331 to measure electrical activity of the muscles of the eye, in accordance with an embodiment of the disclosure. The ophthalmic device 300-A is one possible implementation of the ophthalmic device 200 illustrated in FIG. 2. As illustrated in FIG. 3, the ophthalmic device 300-A includes the enclosure 210, the controller 225, the dynamic optic 230, substrate 329, and the muscle sensor 331. The muscle sensor 331 is an electromyography sensor and includes a first electrode 323, a second electrode 327, and an optional third electrode 333. The substrate 329 may be structural support for the muscle sensor 331 and various components of the ophthalmic device 300-A. In some embodiments, the substrate 329 may be similar to the substrate 215 of FIG. 2. In other embodiments, the substrate 329 may be similar to the rigid center material that is encapsulated by the soft lens material, as described in relation to FIG. 2.

Referring back to FIG. 3A, the dynamic optic 230 is disposed within the central region 301 and coupled to the controller 225 to provide a level of accommodation with the ophthalmic device 300-A based on a signal received or acquired from the muscle sensor 331 representative of the electrical activity of the muscles of the eye. An annular region 315 surrounds the central region 301. The electrodes (e.g., first electrode 323 and second electrode 327) of the muscle sensor 331 are positioned within the annular region 315 to measure electrical activity of the muscles proximate to the annular region 315. In some embodiments, the muscle sensor 331 is an iris muscle sensor (e.g., the iris sensor 235 of FIG. 2) and the annular region 315 overlaps with the iris muscles (e.g., the annulus 114 of FIG. 1) when the ophthalmic device 300-A is mounted on the eye. In other embodiments, the muscle sensor 331 is a ciliary muscle sensor (e.g., the ciliary muscle sensor 240 of FIG. 2) and the annular region 315 overlaps with the ciliary muscles (e.g., the annulus 116 of FIG. 1) when the ophthalmic device 300-A is mounted on the eye.

As illustrated in FIG. 3A, the muscle sensor 331 (e.g., the first electrode 323, the second electrode 327, and the third electrode 333) is coupled to the controller 225. The first electrode 323 and the second electrode 327 form corresponding concentric electrodes that each extend around a central region of the ophthalmic device 300-A. The first electrode 323 is disposed between the central region 301 and the second electrode 327. The third electrode 333 of the muscle sensor 331 may be an optional reference electrode positioned outside of the annular region 315 for differential measurements. Therefore, in some embodiments, the muscle sensor 331 has a bipolar configuration (rather than unipolar) to detect or measure the electrical activity of the muscle with the first electrode 323, the second electrode 327, and the third electrode 333. The bipolar configuration allows for differential measurements, which advantageously may allow for the removal of noise common to both the first electrode 323 and the second electrode 327 due to the third electrode 333. For example, in one embodiment, a first pre-signal corresponds to the measurement or reading from the first electrode 323, a second pre-signal corresponds to the measurement or reading from the second electrode 327, and a reference signal corresponds to measurement or reading from the third electrode 333. A first electrode signal corresponds to the difference between the first pre-signal and the reference signal, while a second electrode signal corresponds to the difference between the second pre-signal and the reference signal. In this embodiment, the first signal of the muscle sensor 331 then corresponds to the difference between the first electrode signal and the second electrode signal. In some embodiments, this may be achieved with a differential amplifier included in the controller 225. The removal of noise may improve the signal to noise ratio of the muscle sensor 331 to increase the measurement accuracy while measuring the electrical activity of the muscles of the eye.

Figure 3B:
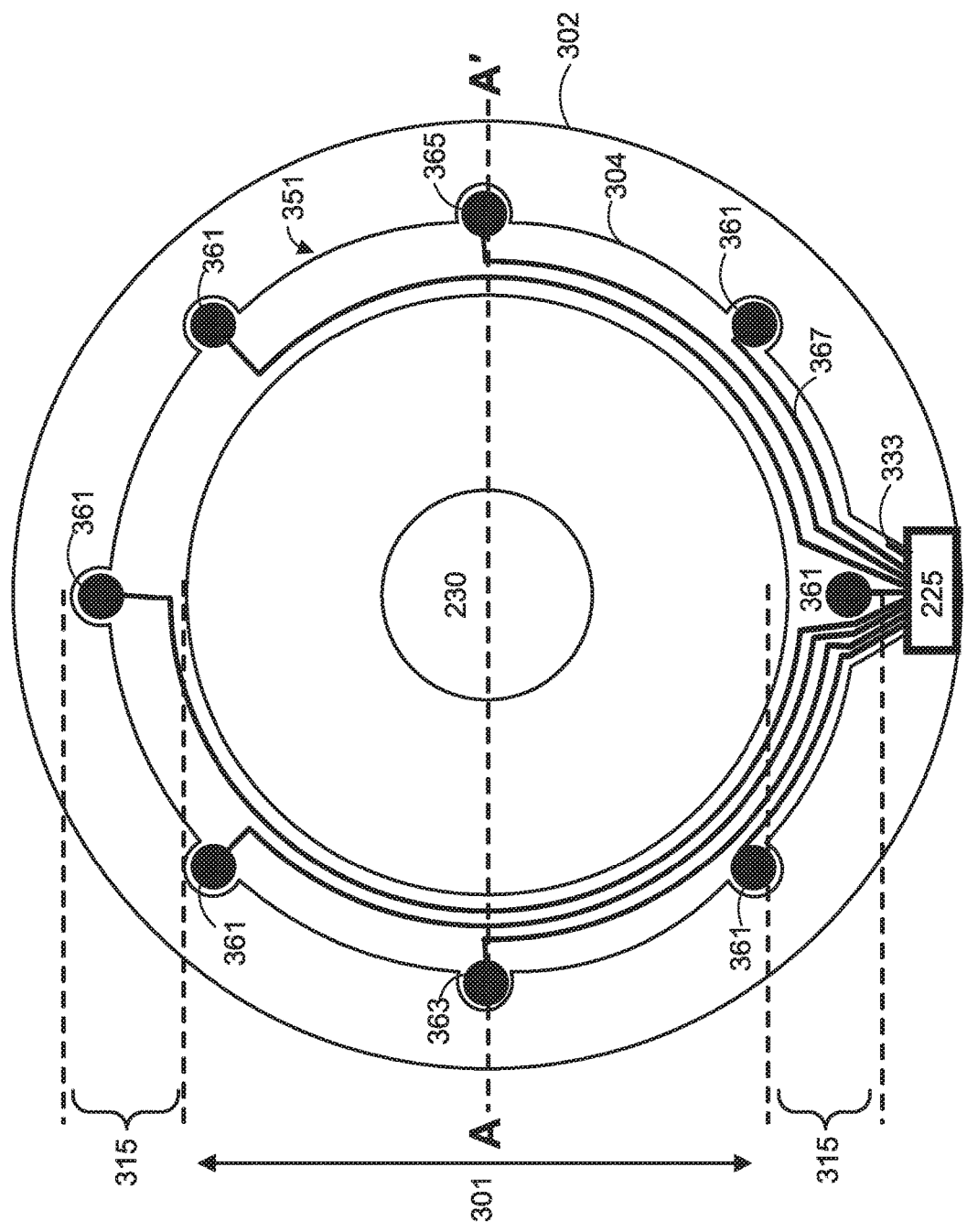
FIG. 3B illustrates a top view of an ophthalmic device with muscle sensor, in accordance with an embodiment of the disclosure.

FIG. 3B illustrates a top view of an ophthalmic device 300-B with muscle sensor 351 to measure electrical activity of the muscles of the eye, in accordance with an embodiment of the disclosure. The ophthalmic device 300-B is one possible implementation of the ophthalmic device 200 illustrated in FIG. 2. As illustrated in FIG. 3, the ophthalmic device 300-B includes an enclosure (e.g., first material 302 encapsulating second material 304), controller 225, dynamic optic 230, and muscle sensor 351. The muscle sensor 351 is an electromyography sensor and includes a plurality of discrete electrodes (including first discrete electrode 363, second discrete electrode 365, and other discrete electrodes 361) coupled to the controller 225 via conductive traces 367. The muscle sensor 351 also includes the optional reference electrode 333. The first material 302 may be a soft lens material (e.g., silicone or silicone-based hydrogels) that encapsulates the second material 304. The second material 304 may be a rigid center material to provide structural support to the various components of the ophthalmic device 300-B (e.g., the muscle sensor 351, the controller 225, and the like). The first material 302 and the second material 304 may be similar or analogous to the first material and second material described in relation to FIG. 2.

Referring back to FIG. 3B, the dynamic optic 230 is disposed within the central region 301 and coupled to the controller 225 to provide a level of accommodation with the ophthalmic device 300-B based on a signal received or acquired from the muscle sensor 351 representative of the electrical activity of the muscles of the eye. Annular region 315 surrounds the central region 301. The plurality of discrete electrodes (e.g., the first discrete electrode 363, the second discrete electrode 365, and the other discrete electrodes 361) of the muscle sensor 351 is positioned proximate to the annular region 315. In some embodiments, the muscle sensor 351 is an iris muscle sensor (e.g., the iris sensor 235 of FIG. 2) and the annular region 315 overlaps with the iris muscles (e.g., the annulus 114 of FIG. 1) when the ophthalmic device 300-B is mounted on the eye. In other embodiments, the muscle sensor 351 is a ciliary muscle sensor (e.g., the ciliary muscle sensor 240 of FIG. 2) and the annular region 315 overlaps with the ciliary muscles (e.g., the annulus 116 of FIG. 1) when the ophthalmic device 300-B is mounted to the eye.

As illustrated in FIG. 3B, the plurality of discrete electrodes (e.g., the first discrete electrode 363, the second discrete electrode 365, the other discrete electrodes 361) is distributed throughout the annular region 315 and coupled to the controller 225 by a corresponding conductive trace 367. A width of the corresponding conductive trace 367 is less than a width of a respective one of the plurality of discrete electrodes. In some embodiments, the plurality of discrete electrodes may have a width or diameter between ten microns and one millimeter. The reference electrode 333 is positioned outside of the annular region 315. In some embodiments, the ophthalmic device 300-B has a bipolar configuration (e.g., when utilizing the optional reference electrode 333) to detect or measure the electrical activity of the muscle with the plurality of discrete electrodes (e.g., the first discrete electrode 363, the second discrete electrode 365, the other discrete electrodes 361) and the reference electrode 333. The bipolar configuration allows for differential measurements, which advantageously may allow for the removal of noise common to the plurality of discrete electrodes (e.g., the first discrete electrode 363 and the second discrete electrode 365) due to the reference electrode 333. The removal of noise may improve the signal to noise ratio of the muscle sensor 351 to increase measurement accuracy while measuring the electrical activity of the muscles of the eye.

Figure 3C:
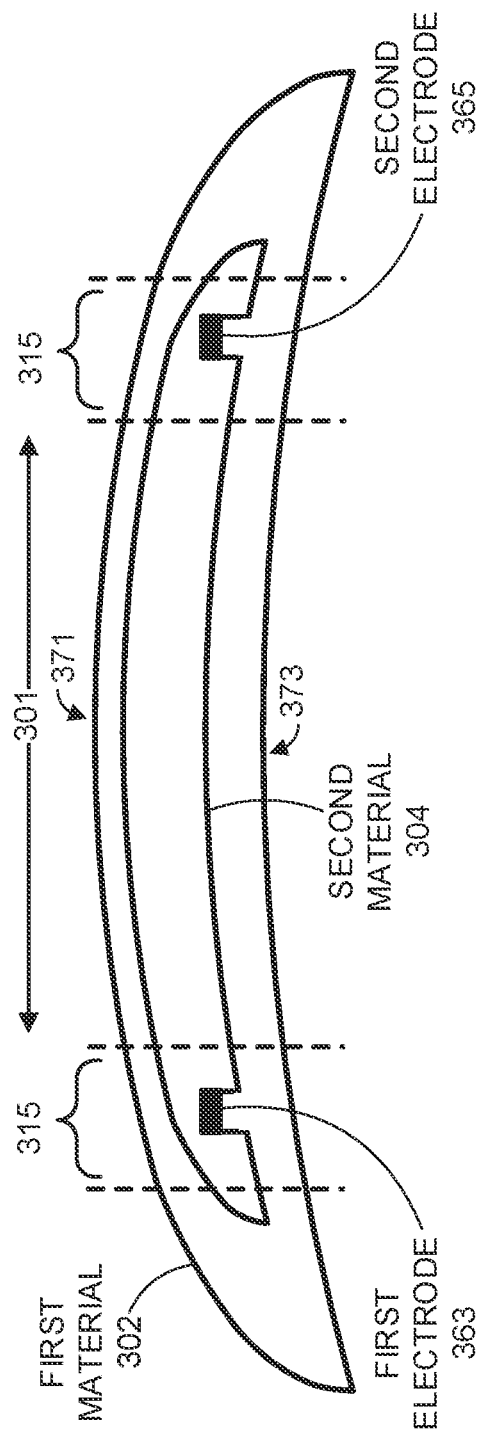
FIG. 3C illustrates a cross-sectional view of the ophthalmic device in FIG. 3B as cut along line A-A', in accordance with an embodiment of the disclosure.

FIG. 3C illustrates a cross-sectional view of the ophthalmic device 300-B in FIG. 3B as cut along line A-A', in accordance with an embodiment of the disclosure. To facilitate contact-mounting of the ophthalmic device 300-B on the eye, the first material 302 includes a convex surface 371 and a concave surface 373. The concave surface 373 is shaped to adhere to a moistened corneal/scleral surface (e.g., by capillary forces with a tear film coating the eye). While mounted to the concave surface 373, the outward-facing surface 371 is shaped to not interfere with eye-lid motion.

An intimate interface between the ocular surface and the ophthalmic device 300-B is of particular importance for achieving accurate measurement of electrical activity of the ocular muscles with the muscle sensor 351. As illustrated, the first discrete electrode 363 and the second discrete electrode 365 are disposed within the second material 304. However, the rigid center of the second material 304 may have a relatively high impedance that makes electrical measurement difficult. Therefore, the plurality of discrete electrodes (e.g., the first discrete electrode 363 and the second discrete electrode 365) may be disposed between at least a portion of the second material 304 and the concave surface 373 of the first material 302. Thus, a surface of the plurality of discrete electrodes has intimate contact with the first material 302, which in turn has intimate contact with the ocular surface when mounted. A low impedance material (e.g., a hydrogel film or coating) may be utilized for the first material 302 to facilitate measurements of the electrical activity of the muscles of the eye. The first material may provide an ideal conductive interface between the plurality of discrete electrodes and the ocular surface. In some embodiments, a separation distance between the plurality of electrodes and the ocular surface is between ten microns to fifty microns. Additionally, it is appreciated that the configuration of the plurality of discrete electrodes (e.g., the positional relationship between the first discrete electrode 363, the first material 302, and the second material 304) may also be utilized in other embodiments of the disclosure (e.g., the ophthalmic device 100 of FIG. 1, ophthalmic device 200 of FIG. 2, and ophthalmic device 300-A of FIG. 3A).

In some embodiments, it is appreciated that measurement or detection of electrical activity may be detected with sensors (e.g., the plurality of discrete electrodes including the first discrete electrode 363 and the second discrete electrode 365) that are contact mounted to the eye. The sensors may subsequently be communicatively coupled (e.g., wirelessly via antenna 245 illustrated in FIG. 2) to an intraocular lens mounted within the eye to adjust accommodation based on the measurements.

In general, it is appreciated that additional electrode configurations and geometries of embodiments of the disclosure may be utilized independently or in combinations thereof suitable for EMG measurements of the iris and ciliary muscles. In particular, the electrodes introduce minimal impact through the visual field by being placed outside of the central field or through miniaturization or optical transparency. It is further appreciated that the electrodes are not strictly limited to the regions in which iris or ciliary muscles directly overlap with the embodiments when mounted. In some embodiments, the electrodes may not overlap with the iris or ciliary muscles while mounted, but measurement of the corresponding electrical activity may still be obtained. This is because the multi-unit depolarization field generated by the iris and ciliary muscles emanate in all directions. However, significant trade-offs such as signal to noise ratio and cross-talk with other signals may be introduced.

Figure 4:
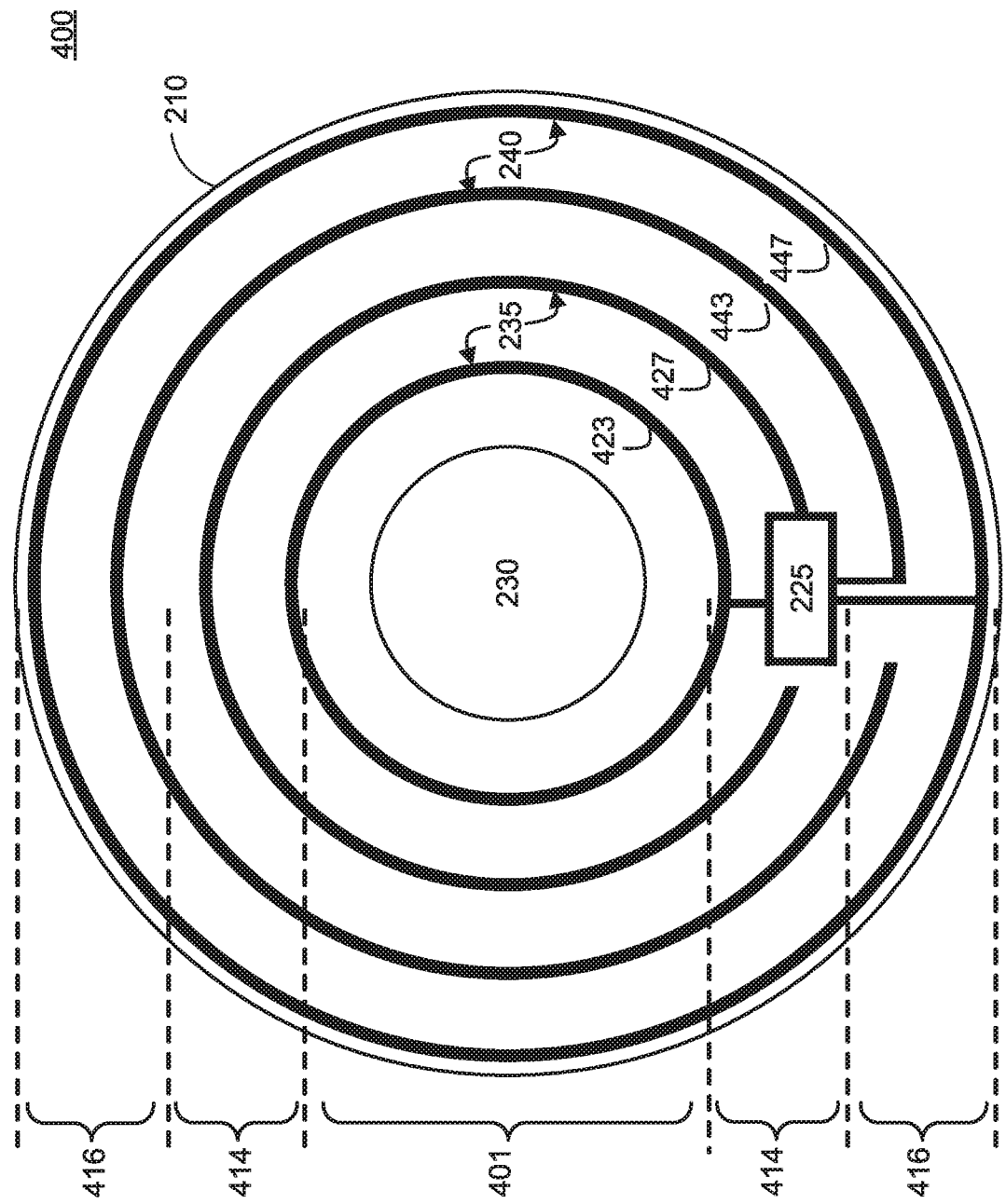
FIG. 4 illustrates a top view of an ophthalmic device 400 with an iris sensor and a ciliary muscle sensor, in accordance with an embodiment of the disclosure.

FIG. 4 illustrates a top view of an ophthalmic device 400 with the iris sensor 235 and the ciliary muscle sensor 240, in accordance with an embodiment of the disclosure. The ophthalmic device 400 is one possible implementation of ophthalmic device 200 of FIG. 2. As illustrated in FIG. 4, the ophthalmic device 400 includes the enclosure 210, the controller 225, the dynamic optic 230, the iris sensor 235, and the ciliary muscle sensor 240. The iris sensor 235 includes a first electrode 423 and a second electrode 427. The ciliary muscle sensor 240 includes a third electrode 443 and a fourth electrode 447. The dynamic optic 230 is disposed within a central region 401. The first electrode 423 and the second electrode 427 are positioned within a first annular region 414 while the third electrode 443 and the fourth electrode 447 are positioned within a second annular region 416. The second annular region 416 is disposed between a perimeter of the ophthalmic device 400 and the first annular region 414.

As illustrated, the first electrode 423 and the second electrode 427 form first concentric electrodes that each extend around the central region 401. The first electrode 423 is positioned between the central region 401 and the second electrode 427. The third electrode 443 and the fourth electrode 447 also form concentric electrodes that each extend around the central region 401. The third electrode 443 is disposed between the first annular region 414 and the fourth electrode 447. It is appreciated that while the electrodes of the iris sensor 235 and the ciliary muscle sensor 240 are illustrated as concentric electrodes, in some embodiments other electrode configuration or geometries may be utilized. In one example, the iris sensor 235 and/or the ciliary muscle sensor 240 may include a plurality of discrete electrodes distributed throughout the first annular region 414 or the second annular region 416, respectively. The plurality of discrete electrodes may be coupled to the controller 225 by a corresponding conductive trace having a width less than the width of a respective one of the plurality of discrete electrodes. This electrode configuration may be similar to the ophthalmic device 300-B illustrated in FIG. 3B.

Referring back to FIG. 4, the iris sensor 235 is an electromyography sensor coupled to the controller 225 to measure first electrical activity of the muscles of the eye proximate to the first annular region 414. Similarly, the ciliary muscle sensor 240 is an electromyography sensor coupled to the controller 225 to measure second electrical activity of the muscles of the eye proximate to the second annular region 416. More specifically, the iris sensor 235 is positioned within the first annular region 414 that surrounds the central region 401 of the ophthalmic device 400 to measure the electrical activity of the iris muscles (e.g., the sphincter and dilator pupillae of the iris). The ciliary muscle sensor 240 is positioned within the second annular region 416 that surrounds both the first annular region 414 and the central region 401 to measure the electrical activity of the ciliary muscle (e.g., brucke fibers and muller fibers). The ophthalmic device 400 may be configured to mount on the eye in a similar manner as ophthalmic device 100 of FIG. 1. For example, when mounted on the eye, the first annular region 414 may overlap the annulus 114 and the second annular region 316 may overlap the annulus 116. Therefore, dimensions of the ophthalmic device 400 of FIG. 4 may be at least partially determined by this degree of overlap. For example, the first annular region 414 may be characterized as an annulus having an inner perimeter diameter of about 4.1 mm and an outer perimeter diameter of about 13.1 mm. Similarly, the second annular region 416 may have an inner perimeter diameter of about 13.1 mm and an outer perimeter diameter of about 20.9 mm.

Thus, in the illustrated embodiment, the ophthalmic device 400 is a sclera lens that extends beyond the corneal surface of the eye to at least partially overlap the scleral surface. However, in other embodiments, the ophthalmic device 400 may have dimensions similar to a contact lens and only partially overlap with the corneal surface. Furthermore, it is appreciated that in some embodiments, certain features may be omitted. For example, in one embodiment, the ophthalmic device 400 may omit the iris sensor 235 and may therefore determine the accommodative effort from the electrical activity of the ciliary muscle. In other embodiments, the ciliary muscle sensor 240 may be omitted and may therefore determine the accommodative effort from the electrical activity of the iris muscles. In this particular embodiment, the ophthalmic device 400 may have dimensions similar to a conventional contact lens as the second annular region 416 may be omitted.

In one embodiment, ophthalmic device 400 is configured to provide closed-loop auto-accommodation of the eye. The controller 225, coupled to the dynamic optic 230, the iris sensor 235, and the ciliary muscle sensor 240, stores instructions that when executed by the controller 225 causes the ophthalmic device 400 to perform operations. These operations include acquiring a first signal representative of the electrical activity of the iris muscles by measuring the electrical activity proximate to the first annular region 414 with the iris sensor 235. A transition in amplitude of the first signal from the iris sensor 235 may be detected to identify pupil constriction of the eye. The pupil constriction of the eye may be associated with an initial accommodative effort by the user (e.g., an attempt to focus the eye at a particular distance). In response to detecting the pupil constriction, the ophthalmic device 400 may activate the ciliary muscle sensor 240 to measure electrical activity of the ciliary muscle proximate to the second annular region 416 with the ciliary muscle sensor 240. The electrical activity of the ciliary muscle may be represented by a second signal acquired with the measurements from the ciliary muscle sensor 240. A second transition in amplitude of the second signal is then utilized to identify an accommodation event of the eye (e.g., an accommodative effort to focus the eye at a particular distance). Then based on the identified second transition, a level of accommodation provided by the dynamic optic 230 may be adjusted proportionally based on a magnitude of the second signal during the accommodation event. In the illustrated embodiment, the ophthalmic device 400 has reduced power consumption by activating the ciliary muscle sensor 240 in response to detecting the pupil constriction relative to continuously powering the ciliary muscle sensor 240.

Figure 5A:
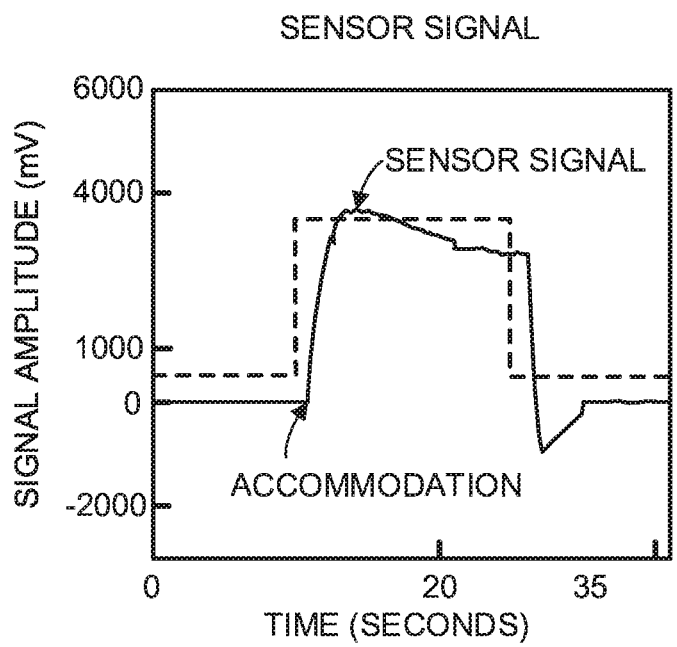
FIGS. 5A-5B illustrate an example output of an electromyography sensor implemented in an ophthalmic device, in accordance with an embodiment of the disclosure.
Figure 5B:
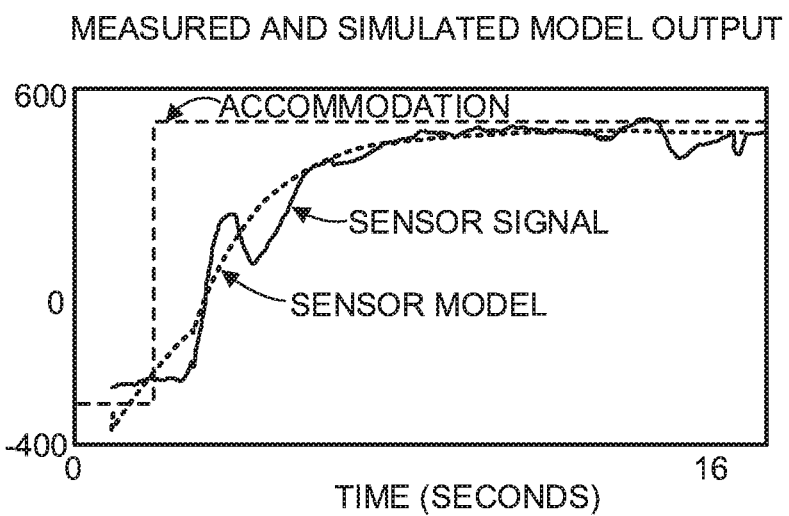

FIGS. 5A-5B illustrate an example output of an electromyography sensor implemented in the ophthalmic devices of FIGS. 1-4. The ophthalmic devices are customized to detect sharp transitions in signal amplitude as illustrated in FIG. 5A. Detecting of this transition in signal amplitude allows for the identification or detection of the accommodation process (e.g., an accommodative effort by the eye of the user). In some embodiments pupil constriction (e.g., with the iris sensor 235 of FIG. 2) will first be detected followed by detection of ciliary muscle activation (e.g., with the ciliary muscle sensor 240 of FIG. 2). Then a proportional integral controller (e.g., controller 225 of FIG. 2) adjusts the focal length (e.g., level of accommodation) provided by the dynamic lens (e.g., the dynamic optic 230 of FIG. 2) proportional to the magnitude of the muscle activation (e.g., determined, at least in part, from the peak in signal amplitude illustrated in FIG. 5A). In other embodiments the pupil constriction and the detection of ciliary muscle activation are achieved with a single electromyography sensor. The single electromyography sensor may be coupled with a controller including a signal classifier to distinguish between the signal response corresponding to the pupil constriction and the ciliary muscle activation.

In some embodiments, a dynamic input-output model (e.g., sensor model illustrated in FIG. 5B) is developed from the input signal (e.g., sensor signal representative of electrical activity of muscles of the eye as illustrated FIG. 5A-5B) to the output of the iris or ciliary muscle response. In one embodiment, the input data is fit via a $4^{th}$ order (4 poles/4 zeros) auto-regressive moving average filter. The resulting input-output model may then be used to obtain a model of the system such as a transfer function or a state-space model to reliably sense the signals from the ciliary muscles and/or iris muscles of the eye. In some embodiments, the transition may refer to a transition or change in amplitude, frequency, and/or phase of the signal to determine or otherwise detect the accommodation process (e.g., accommodative effort, pupil constriction, activation of the ciliary muscle, and the like) of the eye. For example, the transition of the signal may be identified after applying the dynamic input-put model and/or filter to the input data (e.g., the signal from the muscle sensor).

Figure 6A:
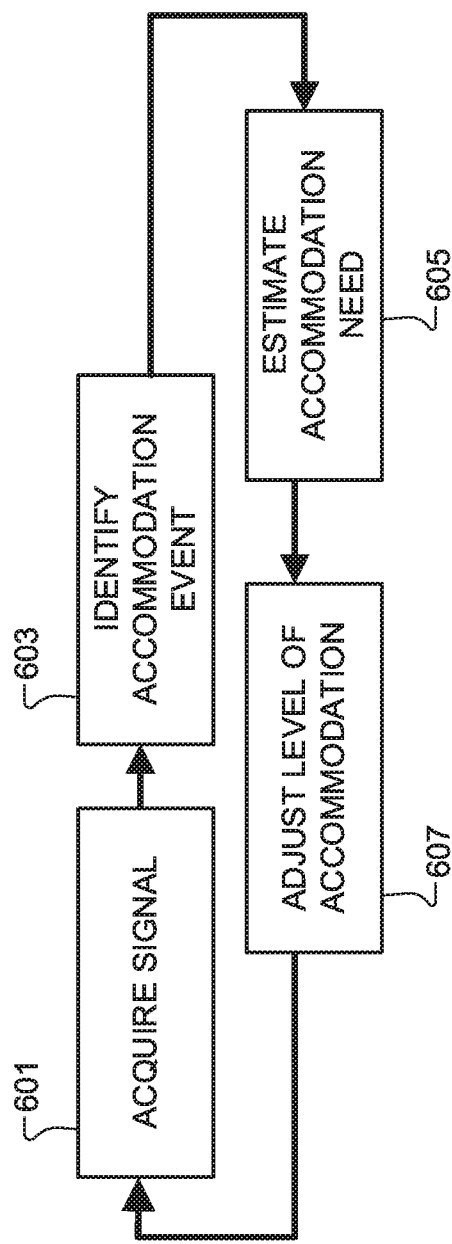
FIG. 6A is a flow-chart describing a method for closed-loop accommodation adjustment of an ophthalmic device, in accordance with an embodiment of the disclosure.

FIG. 6A is a flow-chart describing a method 600 for closed-loop accommodation adjustment of an ophthalmic device (e.g., ophthalmic device 200 of FIG. 2) with a muscle sensor, in accordance with an embodiment of the disclosure. Block 601 illustrates acquiring a first signal representative of the electrical activity of a muscle by measuring the electrical activity with an electromyography sensor. Block 603 then illustrates identifying an accommodation event (e.g., an accommodative effort to adjust the focus of the eye) from the first signal. In some embodiments, the accommodation event may be identified by detecting a transition in amplitude of the first signal from the muscle sensor. Block 605 then illustrates estimating an accommodation need based on the identified accommodation event. In one embodiment, the accommodation need may be estimated, at least in part, based on a first magnitude of the first signal during the identified accommodation event. Block 607 then illustrates adjusting the level of accommodation (e.g., provided by the dynamic optic 230 of the ophthalmic device 200 of FIG. 2) proportionally based on the first magnitude of the first signal. This method may continuously recur such that dynamic vision correction may be provided.

Figure 6B:
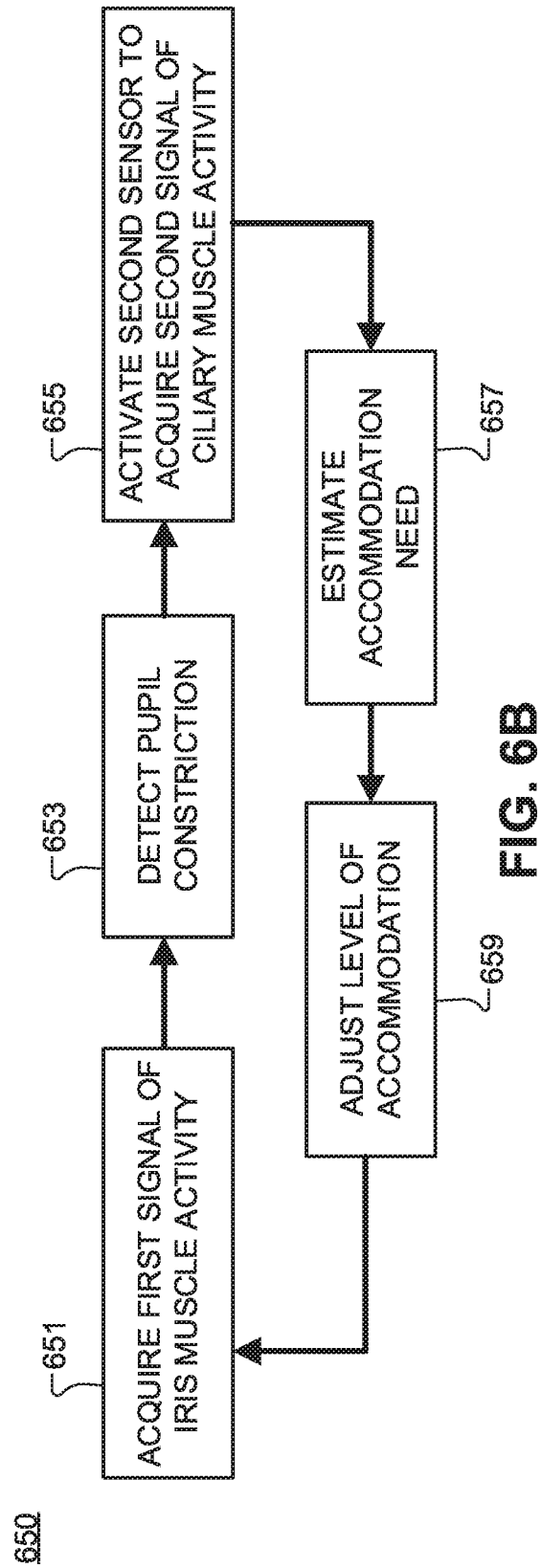
FIG. 6B is a flow-chart describing a method for closed-loop accommodation adjustment of an ophthalmic device with one or more muscle sensors, in accordance with an embodiment of the disclosure.

FIG. 6B is a flow-chart describing a method 650 for closed-loop accommodation adjustment of an ophthalmic device (e.g., ophthalmic device 200 of FIG. 2) with one or more muscle sensors, in accordance with an embodiment of the disclosure. Block 651 illustrates acquiring a first signal representative of the electrical activity of a muscle by measuring the electrical activity with a first sensor (e.g., an iris EMG sensor). In one embodiment, the first signal is representative of iris muscle electrical activity determined from the iris EMG sensor. Block 653 then illustrates detecting pupil constriction based on the first signal. The pupil constriction may be determined by identifying a transition amplitude of the first signal. Block 655 illustrates activating a second sensor (e.g., a ciliary muscle EMG sensor) in response to detecting the pupil constriction of the eye. A second signal from the second sensor is then acquired that is representative of the ciliary muscle electrical activity. Based on the second signal, an accommodation event (e.g., an accommodative effort to adjust the focus of the eye) may be identified. In some embodiments, the accommodation event may be identified by detecting a second transition in amplitude of the second signal from the second sensor. Block 657 then illustrates estimating an accommodation need based on the identified accommodation event. In one embodiment, the accommodation need may be estimated, at least in part, based on a first magnitude of the second signal during the identified accommodation event. Block 659 then illustrates adjusting the level of accommodation (e.g., provided by the dynamic optic 230 of the ophthalmic device 200 of FIG. 2) proportionally based on the first magnitude of the second signal. This method may continuously recur such that dynamic vision correction may be provided.

Figure 7:
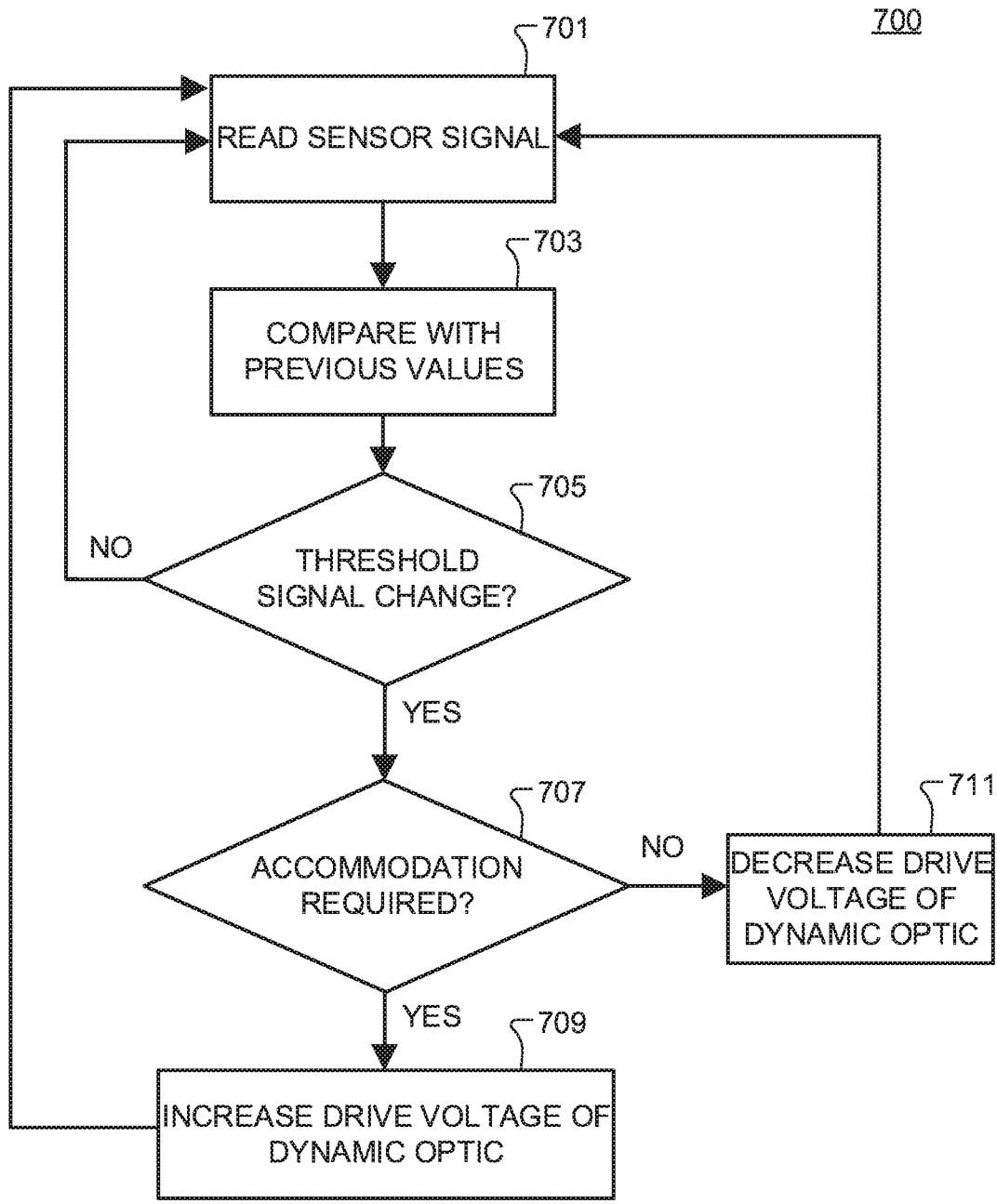
FIG. 7 is a flow-chart describing a method for determining if a change in accommodation provided by an ophthalmic device is necessary, in accordance with an embodiment of the disclosure.

FIG. 7 is a flow-chart describing a method 700 for determining if a change in accommodation provided by the ophthalmic device is necessary, in accordance with an embodiment of the disclosure. In some embodiments, the ophthalmic devices of FIGS. 1-4 may be a closed-loop system that continuously provided auto-accommodation. However, the level of accommodation provided by the ophthalmic devices may only need to change if a specific threshold has been met. This may prevent the ophthalmic devices from inadvertently adjusting the provided accommodation when a change in accommodation is not needed.

Block 701 illustrates reading or acquiring a sensor signal (e.g., a first or second signal representative of the electrical activity of the muscles of the eye). Block 703 then compares the signal from block 701 to previous values (e.g. a previous value of the sensor signal representing a noise threshold). If the sensor signal is less than a threshold signal change the loop proceeds back to block 701. If the sensor signal is greater than the threshold signal change the signal is further analyzed and proceeds to block 707. Block 707 determines whether a change in accommodation provided by the ophthalmic device is required. If the accommodative need is different than the previous accommodation provided by the ophthalmic device it may be determined that a change in accommodation is necessary and the process continues to block 709. Block 709 illustrates increasing the drive voltage of the dynamic optic (e.g., the dynamic optic 230 of FIG. 2). However, if accommodation is not necessary, block 707 proceeds to block 711. Block 711 illustrates decreasing the drive voltage of the dynamic optic. Block 709 or 711 then proceed back to the initial block 701 and the process is repeated.

The processes explained above are described in terms of computer software and hardware. The techniques described may constitute machine-executable instructions embodied within a tangible or non-transitory machine (e.g., computer) readable storage medium, that when executed by a machine (e.g., controller 225) will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device, comprising:
   an enclosure configured to mount in or on an eye, wherein the enclosure includes a first material and a second material disposed within the first material;
   an electromyography (EMG) sensor adapted to measure electrical activity of a muscle of the eye proximate to a first annular region of the ophthalmic device when the ophthalmic device is mounted in or on the eye, wherein the first annular region surrounds a central region of the ophthalmic device, wherein the EMG sensor includes a first electrode and a second electrode, each positioned within the first annular region between the first material and at least a portion of the second material, when the ophthalmic device is viewed from a cross-sectional side view, and wherein the first material is different than the second material; and
   a controller coupled to the EMG sensor, wherein the controller stores instructions that when executed by the controller causes the ophthalmic device to perform operations including:
      acquiring a first signal representative of the electrical activity of the muscle by measuring the electrical activity with the EMG sensor.

2. The ophthalmic device of claim 1, wherein the first electrode and the second electrode form concentric electrodes that extend around the central region of the ophthalmic device within the first annular region, and wherein the first electrode is disposed between the central region and the second electrode.

3. The ophthalmic device of claim 1, wherein the EMG sensor further includes a plurality of discrete electrodes distributed throughout the first annular region including the first electrode and the second electrode, wherein each of the discrete electrodes is coupled to the controller by a conductive trace, and wherein a width of the conductive trace is less than a width of a corresponding one of the discrete electrodes.

4. The ophthalmic device of claim 1, wherein the EMG sensor further includes a reference electrode positioned outside of the first annular region, and wherein the EMG sensor has a bipolar electrode configuration to detect the electrical activity of the muscle with differential measurements via the first electrode, the second electrode, and the reference electrode.

5. The ophthalmic device of claim 1, further comprising:
   a dynamic optic disposed within a central region of the ophthalmic device and surrounded by the first annular region, wherein the dynamic optic is coupled to the controller to provide a level of accommodation for the eye, and wherein the controller includes additional instructions that when executed by the controller causes the ophthalmic device to perform further operations including:
      detecting a transition in amplitude of the first signal from the EMG sensor to identify an accommodation event of the eye; and
      adjusting the level of accommodation provided by the dynamic optic based on a first magnitude of the first signal during the accommodation event.

6. The ophthalmic device of claim 5, wherein the EMG sensor is positioned to measure the electrical activity of a ciliary muscle of the eye or an iris muscle of the eye when the ophthalmic device is mounted in or on the eye.

7. The ophthalmic: device of claim 1, further comprising:
   a second EMG sensor coupled to the controller to measure second electrical activity proximate to a second annular region of the ophthalmic device, wherein the second EMG sensor includes a third electrode and a fourth electrode, each positioned within the second annular region disposed between a perimeter of the ophthalmic device and the first annular region.

8. The ophthalmic device of claim 7, wherein the first annular region and the second annular region are, respectively, positioned proximate to an iris muscle or a ciliary muscle of the eye when the ophthalmic device is mounted in or on the eye, wherein the EMG sensor and the second EMG sensor are respectively adapted to measure iris muscle electrical activity measure ciliary muscle electrical activity.

9. The ophthalmic device of claim 8, wherein the electrical activity corresponds to the iris muscle electrical activity, wherein the controller includes additional instructions that when executed by the controller causes the ophthalmic device to perform further operations including:
   detecting a transition in the first signal from the EMG sensor to identify a pupil constriction of the eye, wherein the transition corresponds to at least one of a change in amplitude, frequency, or phase of the first signal.

10. The ophthalmic device of claim 9, wherein the controller includes additional instructions that when executed by the controller causes the ophthalmic device to perform further operations including:
    in response to detecting the pupil constriction of the eye, activating the second EMG sensor to measure the electrical activity of the ciliary muscle; and
    acquiring a second signal from the second EMG sensor, wherein the second signal is representative of the ciliary muscle electrical activity.

11. The ophthalmic device of claim 10, further comprising:
a dynamic optic disposed within a central region of the ophthalmic device and surrounded by the first annular region, wherein the dynamic optic is coupled to the controller to provide a level of accommodation for the eye, and wherein the controller includes additional instructions that when executed by the controller causes the ophthalmic device to perform farther operations including:
detecting a second transition in amplitude of the second signal from the second EMG sensor to identify an accommodation event of the eye; and
adjusting the level of accommodation based on a first magnitude of the second signal during the accommodation event.

12. The ophthalmic device of claim 8, wherein the third electrode and the fourth electrode form concentric electrodes that extend around the first annular region of the ophthalmic device, and wherein the third electrode is disposed between the first annular region and the fourth electrode.

13. The ophthalmic device of claim 8, wherein the second EMG sensor further includes a plurality of discrete electrodes distributed throughout the second annular region including the third electrode and the fourth electrode, wherein each of the discrete electrodes is coupled to the controller by a conductive trace, and wherein a width of the conductive trace is less than a width of a corresponding one of the discrete electrodes.

14. The ophthalmic device of claim 8, wherein the second EMG sensor further includes a reference electrode positioned outside of the second annular region, and wherein the second EMG sensor has a bipolar electrode configuration to detect the measure ciliary muscle electrical activity differential measurements via the third electrode, the fourth electrode, and the reference electrode.

15. The ophthalmic device of claim 1, wherein the first material is less rigid than the second material, and wherein the first material exhibits ionic conductivity to provide a conductive interface between the EMG sensor and the eye when the ophthalmic device is mounted in or on the eye.

16. The ophthalmic device of claim 1, wherein the first electrode and the second electrode contacts both the first material and the second material.

17. The ophthalmic device of claim 1, wherein the first material exhibits ionic conductivity to provide a conductive interface between the EMG sensor and the eye when the ophthalmic device is mounted in or on the eye, and wherein the first electrode and the second electrode directly contacts the first material.

18. A system for a contact lens, the system comprising:
a central region, a second annular region, and a first annular region disposed between the central region and the second annular region;
a dynamic optic disposed within the central region, the dynamic optic adapted to provide a level of accommodation for an eye when the contact lens is mounted on the eye;
an iris electromyography (EMG) sensor at least partially disposed within the first annular region to measure iris muscle electrical activity of the eye when the contact lens is mounted on the eye;
a ciliary EMG sensor at least partially disposed within the second annular region to measure ciliary muscle electrical activity of the eye when the contact lens is mounted on the eye;
a controller coupled to the dynamic optic, the iris EMG sensor, the ciliary EMG sensor, and a memory, wherein the memory includes instructions that when executed by the controller causes the system to perform operations including:
acquiring a first signal representative of the iris muscle electrical activity with the iris EMG sensor;
detecting a transition in the first signal from the iris EMG sensor to identify a pupil constriction of the eye, wherein the transition includes at least one of a change in amplitude, frequency, or phase of the first signal; and
in response to identifying the pupil constriction, enabling the ciliary EMG sensor to acquire a second signal representative of the ciliary muscle electrical activity.

19. The system of claim 18, wherein the includes additional instructions that when executed by the controller causes the system to perform further operations including:
detecting a second transition in amplitude of the second signal from the ciliary EMG sensor to identify an accommodation event of the eye; and
adjusting the level of accommodation provided by the dynamic optic based on a first magnitude of the second signal during the accommodation event.

20. The system of claim 18, further comprising:
an enclosure configured to mount on the eye, wherein the enclosure includes a first material and a second material disposed within the first material, wherein the iris EMG sensor or the ciliary EMG sensor includes at least a first electrode and a second electrode positioned between the first material and at least a portion of the second material.

21. The system of claim 18, wherein the iris EMG sensor includes at least a first electrode and a second electrode disposed within the first annular region, and wherein the ciliary EMG sensor includes at least a third electrode and fourth electrode disposed within the second annular region.

22. The system of claim 21, wherein the first electrode and the second electrode form concentric electrodes that extend around the central region, and wherein the first electrode is disposed between the second electrode and the central region.

23. The system of claim 22, wherein the third electrode and the fourth electrode form concentric electrodes that extend around the first annular region, and wherein the third electrode is disposed between the second electrode and the fourth electrode.

24. The system of claim 18, wherein the iris EMG sensor or the ciliary EMG sensor further includes a plurality of discrete electrodes distributed respectively throughout the first annular region or the second annular region.

25. At least one non-transitory machine-accessible storage medium that provides instructions that, when executed by a machine, will cause the machine to perform operations comprising:
receiving a first signal representative of an iris muscle electrical activity of an eye, wherein the first signal is generated, at least in part, by measurements from an iris electromyography (EMG) sensor included in an ophthalmic device;
detecting a transition in the first signal to identify a pupil constriction of the eye, wherein the transition includes at least one of a change in amplitude, frequency, or phase of the first signal; and
in response to identifying the pupil constriction, enabling a ciliary EMG sensor included in the ophthalmic device to acquire a second signal representative of the ciliary muscle electrical activity of the eye.

26. The at least one non-transitory machine-accessible storage medium of claim 25, further comprising additional instructions that, when executed by the machine, will cause the machine to perform further operations comprising:
  detecting a second transition in the second signal generated, at least in part, by measurements from the ciliary EMG sensor to identify an accommodation event of the eye; and
  adjusting a level of accommodation provided by a dynamic optic of the ophthalmic device based on a first magnitude of the second signal during the accommodation event.

* * * * *

UNITED STATES PATENT AND TRADEMARK OFFICE
CERTIFICATE OF CORRECTION

PATENT NO. : 11,129,563 B2  
APPLICATION NO. : 16/373533  
DATED : September 28, 2021  
INVENTOR(S) : C. Gutierrez et al.

Page 1 of 1

It is certified that error appears in the above-identified patent and that said Letters Patent is hereby corrected as shown below:

In the Claims

| Column | Line | |
|--------|------|--|
| 18 | 17 | "wherein the includes" to -- wherein the memory includes -- |

Signed and Sealed this  
Tenth Day of May, 2022

Katherine Kelly Vidal  
*Director of the United States Patent and Trademark Office*